(12) United States Patent
Legerton

(10) Patent No.: US 8,894,208 B2
(45) Date of Patent: Nov. 25, 2014

(54) KIT OF HIGHER ORDER ABERRATION CONTACT LENSES AND METHODS OF USE

(71) Applicant: Vicoh, LLC, San Diego, CA (US)

(72) Inventor: Jerome Legerton, San Diego, CA (US)

(73) Assignee: Vicoh, LLC, San Diego, CA (US)

( * ) Notice: Subject to any disclaimer, the term of this patent is extended or adjusted under 35 U.S.C. 154(b) by 6 days.

(21) Appl. No.: 13/853,860

(22) Filed: Mar. 29, 2013

(65) Prior Publication Data

US 2013/0222766 A1    Aug. 29, 2013

Related U.S. Application Data

(63) Continuation-in-part of application No. 12/900,385, filed on Oct. 7, 2010, now Pat. No. 8,430,511.

(51) Int. Cl.
    *A61B 3/00*    (2006.01)
(52) U.S. Cl.
    USPC ............................................. 351/219; 351/247
(58) Field of Classification Search
    USPC ................... 351/200–247, 161, 159, 177
    See application file for complete search history.

(56) References Cited

U.S. PATENT DOCUMENTS

| | | | |
|---|---|---|---|
| 7,131,727 B2 | 11/2006 | Jones et al. | |
| 7,556,381 B2 * | 7/2009 | Kelch et al. | 351/246 |
| 7,731,365 B2 | 6/2010 | Catania et al. | |
| 8,061,843 B2 * | 11/2011 | Kline | 351/247 |
| 8,083,346 B2 | 12/2011 | Legerton | |
| 2003/0107703 A1 * | 6/2003 | Cox et al. | 351/161 |
| 2004/0263782 A1 | 12/2004 | Jones et al. | |
| 2005/0200809 A1 | 9/2005 | Dreher et al. | |
| 2006/0001828 A1 | 1/2006 | Duggan et al. | |
| 2007/0291224 A1 | 12/2007 | Lai | |
| 2008/0231810 A1 | 9/2008 | Catania et al. | |
| 2010/0110382 A1 | 5/2010 | Legerton | |
| 2010/0128224 A1 | 5/2010 | Legerton | |
| 2010/0271569 A1 | 10/2010 | Ohkuma et al. | |
| 2010/0328603 A1 | 12/2010 | Liguori et al. | |

OTHER PUBLICATIONS

European Patent Office, Extended European Search Report, EPO Form 1507S, Feb. 19, 2014, pp. 1-6.

* cited by examiner

*Primary Examiner* — Mohammed Hasan
(74) *Attorney, Agent, or Firm* — Sheppard Mullin Richter & Hampton LLP

(57) ABSTRACT

This application describes a kit of contact lenses comprising two or more contact lenses having a known higher order aberration for each given lens power. By way of example, the higher order aberration may comprise a spherical aberration, a coma aberration, or a trefoil aberration. A practitioner selects a lens from the kit and applies the lens to a patient's eye and measures a residual higher order aberration of the lens-eye system. In cases where the residual higher order aberration exceeds a predetermined magnitude, the practitioner selects a second lens from the kit, applies the second lens to the patient's eye and measures the residual higher order aberration of the lens-eye system.

16 Claims, 2 Drawing Sheets

|         | Base Curve Radius | Power  | Lens Spherical Aberration | Lens Power Increment | Diameter |
|---------|-------------------|--------|---------------------------|----------------------|----------|
| Maximum | 8.40              | +8.00  | 0.15 micron               | 0.25D                | 14.2     |
| Minimum | 8.40              | -12.00 | 0.15 micron               | 0.25 D               | 14.2     |

FIG. 1

|         | Base Curve Radius | Power  | Lens Spherical Aberration | Lens Power Increment | Lens SA increment | Diameter |
|---------|-------------------|--------|---------------------------|----------------------|-------------------|----------|
| Maximum | 8.70              | +8.00  | 0.15 micron               | 0.25D                | 0.15 micron       | 14.2     |
| Minimum | 8.40              | -12.00 | - 0.15 micron             | 0.25 D               | 0.15 micron       | 14.2     |
|         |                   |        |                           |                      |                   |          |

FIG. 2

KIT OF HIGHER ORDER ABERRATION CONTACT LENSES AND METHODS OF USE

REFERENCE TO RELATED APPLICATIONS

This application is a continuation-in-part of U.S. patent application Ser. No. 12/900,385, filed Oct. 7, 2010 Now U.S. Pat. No. 8,430,511 B2, the content of which is incorporated herein by reference in its entirety.

TECHNICAL FIELD

The invention relates generally to contact lenses, and more particularly to a kit of higher order aberration contact lenses and methods of use.

DESCRIPTION OF THE RELATED ART

Contact lenses with optics designed to correct low order aberrations are available in several classes of materials and in a multitude of designs. Such lenses were first manufactured in rigid non-gas permeable material. Hydrogel materials have also been used successfully along with rigid gas permeable materials. Each of these classes of materials have advanced to offer ultra-high oxygen permeability. More recently, the two classes of materials have been combined in composite or hybrid lenses to create lenses with rigid gas permeable centers which are bonded to hydrogel peripheral skirts.

Heretofore, all of these commercialized lenses have been designed and manufactured with optics to correct low order aberrations. For example, U.S. Pat. No. 6,086,204 to Magnante discloses methods for measuring the lens-eye system with predicate lenses for the purpose of manufacturing lenses with higher order aberration correction. The methods are limited to producing a unique lens for each individual eye of a patient. In other words, a contact lens produced using Magante's method provides a custom solution based upon the patient's unique eye characteristics. Other known methods include those for measuring the registration and marking hybrid lenses intended for the correction of higher order aberrations. To date, however, no such lenses have been commercialized.

In view of the above, there remains a need to provide correction for higher order aberrations. The single higher order aberration having the greatest incidence and clinical significance is spherical aberration. By the selection of anterior and posterior curves in a contact lens design, each lens will have a predicted spherical aberration which is added to the unique aberration of the eye upon which it is applied. (See, e.g., *Spherical Aberration of Aspheric Contact Lenses on Eye*, Hammer and Holden, Optometry and Vision Science, 1994). In some cases, the spherical aberration of the lens will add to the spherical aberration of the eye, while in other cases the spherical aberration of the lens will subtract or cancel out the spherical aberration of the eye.

The analysis of the measurements of the spherical aberration of the human eye demonstrates a range from negative to positive values centered on a low positive amount of spherical aberration. An analysis of contact lenses for the correction of low order refractive errors also demonstrates a range from negative to positive values. Some products have been reported to have different amounts of lens spherical aberration across the power range offered in the product. The resultant spherical aberration of a finished lens in air and on the eye can be modulated by the selection of radii of curvature and the degree of asphericity of the surfaces. Even so, it appears that little effort has been directed to select an ideal spherical aberration and to hold such a value constant across the power range of commercialized products.

As a result, the lens selected by a practitioner may fortuitously have a desired spherical aberration to cancel the aberration of a specific eye or conversely have an undesired spherical aberration that will add to the spherical aberration of a specific eye. In general, the prevalence of aberrometers in eye care practitioners' offices is growing. Even so, there is a paucity of evidence in the literature of the recommendation to measure the residual aberrations of the lens eye system for the purpose of selecting a lens which will have the lowest residual spherical aberration or a specific spherical aberration.

BRIEF SUMMARY OF EMBODIMENTS OF THE INVENTION

Embodiments of the present invention are directed toward a kit containing two or more lenses having known higher order aberration values for each given lens power. Such higher order aberration values may include spherical aberration values, coma values and trefoil values. Methods for using the kit are also provided. In operation, an eye care practitioner is able to select lenses from the kit and measure the residual higher order aberration of the lens-eye system. In the event the residual aberrations are positive or negative, or of an undesired magnitude, a second lens could be selected and applied to the eye, and the residual aberrations could again be measured and the process repeated until a final lens is selected that provides the targeted direction and magnitude of spherical aberration and/or coma and/or trefoil.

Unlike the conventional methods set forth hereinabove, embodiments of the present invention do not require customization for any or all higher order aberrations. Moreover, the use of the kit containing a set of lenses having known higher order aberration values for each given lens power allows for same day dispensing of lenses from the kit with a resultant desired spherical aberration correction.

One embodiment of the invention is directed toward a kit of contact lenses, comprising two or more contact lenses, each lens having a known higher order aberration and lens power, wherein the higher order aberration comprises a coma aberration. The kit can include at least one lens of each incremental low order power. In some implementations, the lenses are configured to have at least one base curve, one diameter, a series of low order aberration lens powers, and an increment of difference in lens power between lenses. Additionally, each lens can be marked with a code defining its base curve radius, diopter power, magnitude of trefoil aberration and the trefoil aberration orientation, wherein each lens is marked using laser markings, color markings or silk screen images. In further embodiments, the kit comprises two or more lenses of various low order powers that are manufactured to have two or more different known coma aberrations. The kit may also comprise two or more lenses that are manufactured to have two or more base curves and two or more diameters.

Another embodiment of the invention is directed toward a kit of contact lenses, comprising two or more contact lenses, each lens having a known higher order aberration and lens power, wherein the higher order aberration comprises a trefoil aberration. The kit can include at least one lens of each incremental low order power. In some implementations, the lenses are configured to have at least one base curve, one diameter, a series of low order aberration lens powers, and an increment of difference in lens power between lenses. Additionally, each lens can be marked with a code defining its base curve radius, diopter power, and spherical aberration, wherein each lens is marked using laser markings, color markings or silk screen images. In further embodiments, the kit comprises two or more lenses of various low order powers that are manufactured to have two or more different known trefoil aberrations. The kit may also comprise two or more lenses that are manufactured to have two or more base curves and two or more diameters.

A further embodiment of the invention is directed toward a kit of contact lenses, comprising two or more contact lenses, each lens having two or more known higher order aberrations and lens power, wherein the two or more known higher order aberrations include a spherical aberration. The two or more known higher order aberrations may further include a coma aberration or a trefoil aberration. In addition, the kit of contact lenses can include at least one lens of each incremental low order power. The lenses can be configured to have at least one base curve, one diameter, a series of low order aberration lens powers, and an increment of difference in lens power between lenses. Additionally, each lens can be marked with a code defining its base curve radius, diopter power, the magnitude of the coma aberration and the coma aberration orientation, wherein each lens is marked using laser markings, color markings or silk screen images. In further embodiments, the kit can comprise two or more lenses of various low order powers that are manufactured to have two or more different known coma or trefoil aberrations.

In one implementation of the kit with lenses having two or more higher order aberrations, each lens is marked with a code defining its base curve radius, diopter power, magnitude of spherical aberration, magnitude of coma aberration and the orientation of the coma aberration, wherein each lens is marked using laser markings, color markings or silk screen images. In another implementation, each lens is marked with a code defining its base curve radius, diopter power, magnitude of spherical aberration, magnitude of trefoil aberration and the orientation of the trefoil aberration, wherein each lens is marked using laser markings, color markings or silk screen images. In addition, the kit can comprise two or more lenses that are manufactured to have two or more base curves and two or more diameters.

Another embodiment of the invention is directed toward a kit of contact lenses, comprising two or more contact lenses having a known higher order aberration for each given lens power. By way of example, the higher order aberration may comprise a spherical aberration, a coma aberration, or a trefoil aberration. A practitioner selects a lens from the kit and applies the lens to a patient's eye and measures a residual higher order aberration of the lens-eye system. In cases where the residual higher order aberration exceeds a predetermined magnitude, the practitioner selects a second lens from the kit, applies the second lens to the patient's eye and measures the residual higher order aberration of the lens-eye system. In some embodiments of the invention, the residual higher order aberration of the lens-eye system comprises a positive and/or a negative spherical aberration between zero and 0.15 microns over 6 millimeters.

In one implementation, the kit of contact lenses includes at least one lens of each incremental low order power. The lenses may be configured to have at least one base curve, one diameter, a series of low order aberration lens powers, and an increment of difference in lens power between lenses. In certain embodiments, each lens is manufactured to have a known spherical aberration. Each lens may then be marked with a code defining its base curve radius, diopter power, and spherical aberration. By way of example, the lenses may be marked using laser markings, color markings or silk screen images.

Additional embodiments of the invention may feature a kit of contact lenses comprising two or more lenses of various low order powers that are manufactured to have two or more different known higher order aberrations.

Further embodiments of the invention may feature a kit of contact lenses comprising two or more lenses that are manufactured to have two or more base curves and two or more diameters Another embodiment of the invention comprises a method for using a kit of contact lenses, comprising: selecting a lens from the kit and applying the lens to a patient's eye; measuring a residual higher order aberration of the lens-eye system; if the residual higher order aberration of the lens-eye system is not of a desired direction or magnitude, selecting a second lens from the kit and, applying the lens to the patient's eye and measuring the residual higher order aberration of the lens-eye system; and if the residual higher order aberration of the lens-eye system is of a desired direction and magnitude, selecting the lens as the final lens for the patient's eye.

Other features and aspects of the invention will become apparent from the following detailed description, taken in conjunction with the accompanying drawings, which illustrate, by way of example, the features in accordance with embodiments of the invention. The summary is not intended to limit the scope of the invention, which is defined solely by the claims attached hereto.

BRIEF DESCRIPTION OF THE DRAWINGS

The present invention, in accordance with one or more various embodiments, is described in detail with reference to the following figures. The drawings are provided for purposes of illustration only and merely depict typical or example embodiments of the invention. These drawings are provided to facilitate the reader's understanding of the invention and shall not be considered limiting of the breadth, scope, or applicability of the invention. It should be noted that for clarity and ease of illustration these drawings are not necessarily made to scale.

FIG. 1 is a table comprising the configuration of a sample kit of contact lenses having known spherical aberration values for each given lens power.

FIG. 2 is a table comprising another configuration of a sample kit of contact lenses having two or more lenses of various powers which are manufactured to have two or more different values of spherical aberration correction.

Figure 3:
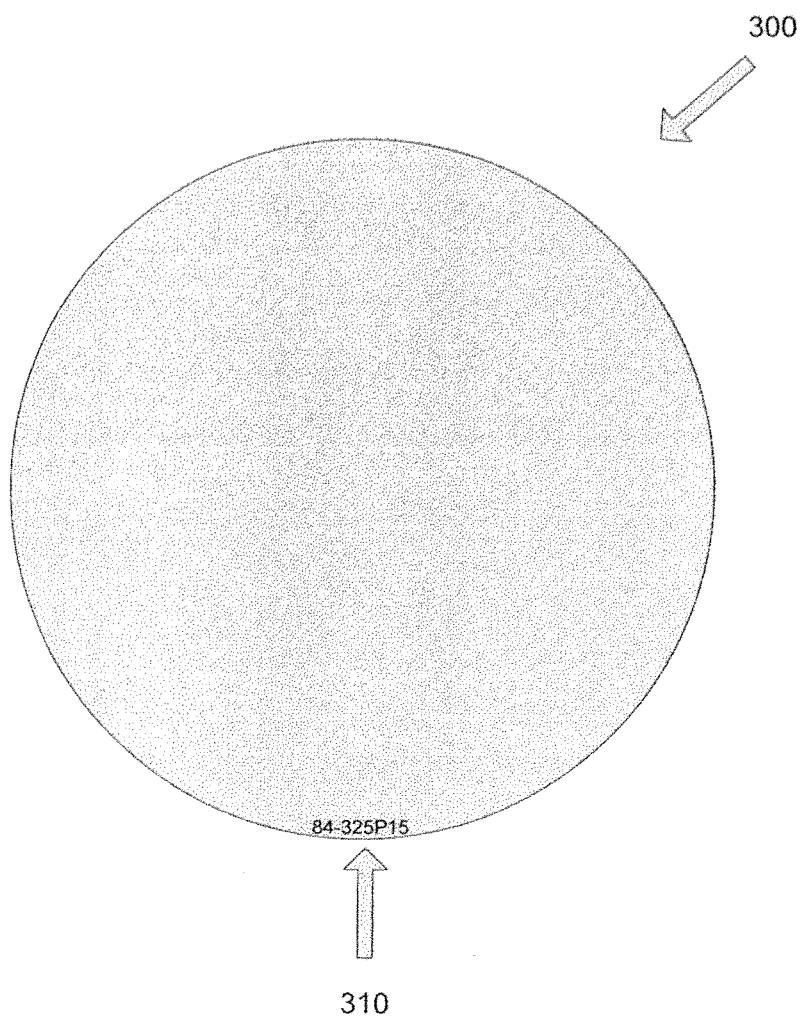
FIG. 3 illustrates a sample laser mark that can be parsed to determine the parameters of the lens.

The figures are not intended to be exhaustive or to limit the invention to the precise form disclosed. It should be understood that the invention can be practiced with modification and alteration, and that the invention be limited only by the claims and the equivalents thereof.

DETAILED DESCRIPTION OF THE EMBODIMENTS OF THE INVENTION

Embodiments of the invention are directed toward a kit containing two or more lenses having known higher order aberration values such as spherical, coma and trefoil aberration values, for each given lens power. In further embodiments of the invention, methods for using the kit of lenses are also provided. In operation, an eye care practitioner is able to select lenses from the kit and measure the residual higher order aberrations of the lens-eye system. In the event a residual aberration is positive or negative, or of an undesired magnitude, a second lens could be selected and applied to the eye, and the residual aberrations could again be measured and the process repeated until a final lens is selected that provides the targeted direction and magnitude of higher order aberrations such as spherical aberration, coma and trefoil.

As set forth herein, various higher order aberrations, such as spherical, coma and trefoil aberrations, may be treated using the kit of lenses. It should be noted that correcting spherical aberrations is generally much easier than correcting other higher order aberrations. In particular, coma and trefoil have the added dimension of having an axis or an orientational specification, while spherical aberration does not. For this reason, embodiments of the invention for the correction of coma and trefoil require orientationally stable lenses and include a predetermined orientation relative to a position on the lens. Although the exemplary embodiments described below may be specifically directed toward the correction of spherical aberrations, the kit of lenses may also contain lenses specifically adapted for the correction of other higher order aberrations such as coma and trefoil. In addition, various lenses may be configured for the correction of any combination of higher order aberrations.

In most instances, a desired residual spherical aberration correction of the lens-eye system is between zero and 0.15 microns over 6 millimeters. By contrast, the range of aberrations for the normal population is between 0.25 microns over 6 millimeters negative spherical aberration to 0.35 microns over 6 mm positive spherical aberration. This range provides the construct for the design of the kit of lenses set forth herein.

In one embodiment of the invention, the kit of contact lenses includes at least one lens of each incremental low order power. Additionally, each lens is manufactured to have a known spherical aberration, and each lens is marked accordingly, for example using laser markings, color markings or silk screen images. The lenses in the kit may be configured to have at least one base curve, one diameter, a series of low order aberration lens powers, and an increment of difference in lens power between lenses. The kit of lenses includes a minimum power and a maximum power for the range of the series. By way of example, FIG. 1 provides a table 100 comprising the configuration of a sample kit of contact lenses having known spherical aberration values for each given lens power. The table 100 indicated that the kit includes lenses having a single base curve radius of 8.4 mm, a power ranging from +8 to −12, a spherical aberration of 0.15 micron, a lens power increment of 0.25 diopters and a diameter of 14.2 mm.

According to the invention, a further embodiment of the kit comprises two or more lenses of various low order powers that are manufactured to have two or more different known spherical aberrations. In various embodiments, the kit may contain lenses in a series of each incremental power or may skip some powers within the range. Additionally, the spherical aberrations of each low order power may be the same throughout the range or may vary throughout the range. FIG. 2 provides a table 200 comprising another configuration of a sample kit of contact lenses having two or more lenses of various powers which are manufactured to have two or more different values of spherical aberration correction. The table 200 indicates that the kit includes lenses having a base curve radius ranging from 8.4 mm to 8.7 mm, a power ranging from +8 to −12, a spherical aberration ranging from 0.15 micron to −0.15 micron, a lens power increment of 0.25 diopters, a spherical aberration increment of 0.15 micron and a diameter of 14.2 mm.

An additional embodiment of the kit comprises two or more lenses that are manufactured to have two or more base curves and/or two or more diameters. Each lens type includes a series of lenses with different low order powers having known spherical aberration values for each given lens power.

According to some embodiments, the lenses in the kit are labeled to help the eye care practitioner use and navigate within the kit when applying lenses to a patient's eyes and measuring the residual lens-eye system aberrations. The lenses themselves can be laser marked or marked by way of silk screen images or by way of color markings, which can be interpreted by the practitioner to decode the parameters of the lens. FIG. 3 illustrates a contact lens 300 having a laser mark 310 that can be parsed to determine the parameters of the lens. In this particular implementation, the laser mark, "84-325P15," is parsed, decoded and/or decrypted by the practitioner to define the contact lens 300 having an 8.40 mm base curve radius, a −3.25 diopter power, and a positive 0.15 micron spherical aberration.

While various embodiments of the present invention have been described above, it should be understood that they have been presented by way of example only, and not of limitation. Likewise, the various diagrams may depict an example architectural or other configuration for the invention, which is done to aid in understanding the features and functionality that can be included in the invention. The invention is not restricted to the illustrated example architectures or configurations, but the desired features can be implemented using a variety of alternative architectures and configurations. Indeed, it will be apparent to one of skill in the art how alternative functional, logical or physical partitioning and configurations can be implemented to implement the desired features of the present invention. Also, a multitude of different constituent module names other than those depicted herein can be applied to the various partitions. Additionally, with regard to flow diagrams, operational descriptions and method claims, the order in which the steps are presented herein shall not mandate that various embodiments be implemented to perform the recited functionality in the same order unless the context dictates otherwise.

Although the invention is described above in terms of various exemplary embodiments and implementations, it should be understood that the various features, aspects and functionality described in one or more of the individual embodiments are not limited in their applicability to the particular embodiment with which they are described, but instead can be applied, alone or in various combinations, to one or more of the other embodiments of the invention, whether or not such embodiments are described and whether or not such features are presented as being a part of a described embodiment. Thus, the breadth and scope of the present invention should not be limited by any of the above-described exemplary embodiments.

Terms and phrases used in this document, and variations thereof, unless otherwise expressly stated, should be construed as open ended as opposed to limiting. As examples of the foregoing: the term "including" should be read as meaning "including, without limitation" or the like; the term "example" is used to provide exemplary instances of the item in discussion, not an exhaustive or limiting list thereof; the terms "a" or "an" should be read as meaning "at least one," "one or more" or the like; and adjectives such as "conventional," "traditional," "normal," "standard," "known" and terms of similar meaning should not be construed as limiting the item described to a given time period or to an item available as of a given time, but instead should be read to encompass conventional, traditional, normal, or standard technologies that may be available or known now or at any time in the future. Likewise, where this document refers to technologies that would be apparent or known to one of ordinary skill in the art, such technologies encompass those apparent or known to the skilled artisan now or at any time in the future.

The presence of broadening words and phrases such as "one or more," "at least," "but not limited to" or other like phrases in some instances shall not be read to mean that the narrower case is intended or required in instances where such broadening phrases may be absent. The use of the term "module" does not imply that the components or functionality described or claimed as part of the module are all configured in a common package. Indeed, any or all of the various components of a module, whether control logic or other components, can be combined in a single package or separately maintained and can further be distributed in multiple groupings or packages or across multiple locations.

Additionally, the various embodiments set forth herein are described in terms of exemplary block diagrams, flow charts and other illustrations. As will become apparent to one of ordinary skill in the art after reading this document, the illustrated embodiments and their various alternatives can be implemented without confinement to the illustrated examples. For example, block diagrams and their accompanying description should not be construed as mandating a particular architecture or configuration.

The invention claimed is:

1. A kit of contact lenses, comprising:
   two or more contact lenses, each lens having a known higher order aberration and lens power; wherein the kit includes at least one lens of each incremental low order power; wherein the higher order aberration comprises a coma aberration;
   wherein the lenses are configured to have at least one base curve, one diameter, a series of low order aberration lens powers, and an increment of difference in lens power between lenses.

2. The kit of claim 1, wherein the kit comprises two or more lenses of various low order powers that are manufactured to have two or more different known coma aberrations.

3. The kit of claim 1, wherein the kit comprises two or more lenses that are manufactured to have two or more base curves and two or more diameters.

4. A kit of contact lenses, comprising:
   two or more contact lenses, each lens having a known higher order aberration and lens power;
   wherein the higher order aberration comprises a coma aberration;
   wherein each lens is marked with a code defining its base curve radius, diopter power, the magnitude of the coma aberration and the coma aberration orientation, wherein each lens is marked using laser markings, color markings or silk screen images.

5. A kit of contact lenses, comprising: two or more contact lenses, each lens having a known higher order aberration and lens power;
   wherein the kit includes at least one lens of each incremental low order power; wherein the higher order aberration comprises a trefoil aberration; wherein the lenses are configured to have at least one base curve, one diameter, a series of low order aberration lens powers, and an increment of difference in lens power between lenses.

6. The kit of claim 5, wherein the kit comprises two or more lenses of various low order powers that are manufactured to have two or more different known trefoil aberrations.

7. The kit of claim 5, wherein the kit comprises two or more lenses that are manufactured to have two or more base curves and two or more diameters.

8. A kit of contact lenses, comprising:
   two or more contact lenses, each lens having a known higher order aberration and lens power;
   wherein the higher order aberration comprises a trefoil aberration;
   wherein each lens is marked with a code defining its base curve radius, diopter power, magnitude of trefoil aberration and the trefoil aberration orientation, wherein each lens is marked using laser markings, color markings or silk screen images.

9. A kit of contact lenses, comprising:
   two or more contact lenses, each lens having two or more known higher order aberrations and lens power;
   wherein the kit includes at least one lens of each incremental low order power;
   wherein the two or more known higher order aberrations include a spherical aberration.

10. The kit of claim 9, wherein the two or more known higher order aberrations further include a coma aberration.

11. The kit of claim 9, wherein the two or more known higher order aberrations further include a trefoil aberration.

12. The kit of claim 9, wherein the lenses are configured to have at least one base curve, one diameter, a series of low order aberration lens powers, and an increment of difference in lens power between lenses.

13. The kit of claim 12, wherein the kit comprises two or more lenses of various low order powers that are manufactured to have two or more different known coma or trefoil aberrations.

14. The kit of claim 12, wherein the kit comprises two or more lenses that are manufactured to have two or more base curves and two or more diameters.

15. The kit of claim 9, wherein each lens is marked with a code defining its base curve radius, diopter power, magnitude of spherical aberration, magnitude of trefoil aberration and the orientation of the trefoil aberration, wherein each lens is marked using laser markings, color markings or silk screen images.

16. A kit of contact lenses, comprising:
   two or more contact lenses, each lens having two or more known higher order aberrations and lens power;
   wherein the two or more known higher order aberrations include a spherical aberration wherein each lens is marked with a code defining its base curve radius, diopter power, magnitude of spherical aberration, magnitude of coma aberration and the orientation of the coma aberration, wherein each lens is marked using laser markings, color markings or silk screen images.

* * * * *